United States Patent
Gregg

(10) Patent No.: US 11,013,469 B2
(45) Date of Patent: May 25, 2021

(54) AUTOMATIC CLASSIFICATION/INTEPRETATION OF ECG WAVES FOR NON-ATHLETES/ATHLETES

(71) Applicant: KONINKLIJKE PHILIPS N.V., Eindhoven (NL)

(72) Inventor: Richard Earl Gregg, Westford, MA (US)

(73) Assignee: Koninklijke Philips N.V., Eindhoven (NL)

( * ) Notice: Subject to any disclaimer, the term of this patent is extended or adjusted under 35 U.S.C. 154(b) by 112 days.

(21) Appl. No.: 16/069,965

(22) PCT Filed: Jan. 10, 2017

(86) PCT No.: PCT/EP2017/050418
§ 371 (c)(1),
(2) Date: Jul. 13, 2018

(87) PCT Pub. No.: WO2017/121729
PCT Pub. Date: Jul. 20, 2017

(65) Prior Publication Data
US 2019/0015051 A1    Jan. 17, 2019

Related U.S. Application Data

(60) Provisional application No. 62/278,529, filed on Jan. 14, 2016.

(51) Int. Cl.
A61B 5/00 (2006.01)
A61B 5/316 (2021.01)
(Continued)

(52) U.S. Cl.
CPC .......... *A61B 5/7264* (2013.01); *A61B 5/0245* (2013.01); *A61B 5/02405* (2013.01);
(Continued)

(58) Field of Classification Search
CPC ........ A61B 5/02–0295; A61B 2503/10; A61B 5/02405; A61B 5/0245; A61B 5/04012;
(Continued)

(56) References Cited

U.S. PATENT DOCUMENTS

| 2010/0168578 | A1 | 7/2010 | Garson et al. |
| 2016/0287166 | A1* | 10/2016 | Tran ........................ H04W 4/80 |
| 2017/0000366 | A1 | 1/2017 | Gregg |

OTHER PUBLICATIONS

Wikipedia, Athletic heart syndrome, 2020, https://en.wikipedia.org/wiki/Athletic_heart_syndrome (Year: 2020).*

(Continued)

*Primary Examiner* — Jonathan T Kuo

(57) ABSTRACT

An electrocardiogram diagnostic system (30) having a non-athletic ECG diagnostic mode and an athletic ECG diagnostic mode. The electrocardiogram diagnostic system (30) employs an electrocardiogram wave controller (30) and an electrocardiogram diagnostic controller (50). In operation, the electrocardiogram wave controller (30) generates an ECG wave responsive to one or more electrode signals. In response thereto, the electrocardiogram diagnostic controller (50) classifies the ECG wave as either a non-athletic ECG wave or an athletic ECG wave, interprets a non-athletic classified ECG wave based on non-athletic ECG diagnostic criteria as either a normal non-athletic ECG wave or an abnormal non-athletic ECG wave, and interprets an athletic classified ECG wave based on athletic ECG diagnostic criteria as either a normal athletic ECG wave or an abnormal athletic ECG wave.

20 Claims, 7 Drawing Sheets

(51) Int. Cl.
    *A61B 5/318*     (2021.01)
    *A61B 5/364*     (2021.01)
    *A61B 5/024*     (2006.01)
    *A61B 5/0245*     (2006.01)

(52) U.S. Cl.
    CPC .............. *A61B 5/316* (2021.01); *A61B 5/318* (2021.01); *A61B 5/364* (2021.01); *A61B 5/7267* (2013.01); *A61B 2503/10* (2013.01)

(58) Field of Classification Search
    CPC ...... A61B 5/0402–0472; A61B 5/0468; A61B 5/7264; A61B 5/7267
    See application file for complete search history.

(56) References Cited

OTHER PUBLICATIONS

Corrado et al., "Recommendations for interpretation of 12-lead electrocardiogram in the athlete", European Heart Journal, vol. 31, No. 2 (2009), pp. 243-259.

\* cited by examiner

AUTOMATIC CLASSIFICATION/INTEPRETATION OF ECG WAVES FOR NON-ATHLETES/ATHLETES

This application is a national stage application under 35 U.S.C. § 371 of International Application No. PCT/EP2017/050418 filed on Jan. 10, 2017 and published in the English language on Jul. 20, 2017 as International Publication No. WO2017/121729, which claims priority to U.S. Patent Application No. 62/278,529 filed on Jan. 14, 2016, the entire disclosures of which are incorporated herein by reference.

FIELD OF THE INVENTION

The present disclosure generally relates to differing diagnoses of an ECG wave for non-athlete and an ECG wave for an athlete. The present disclosure specifically relates to classifying an ECG wave as non-athletic or athletic, and interpreting the ECG wave as being normal or abnormal based on the non-athlete/athlete classification.

BACKGROUND OF THE INVENTION

An electrocardiogram (ECG) as known in the art increases an ability to detect abnormal cardiovascular conditions (e.g., cardiomyopathies) that may lead to sudden cardiac arrest (SCD). An issue with interpreting an ECG for an athlete is regular, intense physical training has been associated with electrical manifestations in a heart of the athlete that are reflected by an increase in a vagal tone and an enlargement of a cardiac chamber of the athletic heart.

An increase in vagal tone of the athletic heart results in ECG manifestations (e.g., sinus bradycardia, sinus arrhythmia, first-degree atrioventricular (AV) block and Morbitz type I second-degree AV block) that would be considered abnormal in the general population if athletic training were not taken into account during an ECG diagnosis.

Similarly, an enlargement of a cardiac chamber of the athletic heart results in ECG manifestations (e.g., left ventricular hypertrophy and/or acute myocardial infraction) that would be considered abnormal in the general population if athletic training were not taken into during an ECG diagnosis.

SUMMARY OF THE INVENTION

The present disclosure provides systems, devices, controllers and methods to minimize, if not prevent, false positive abnormal ECG interpretations of highly trained athletes.

Generally, the present disclosure is premised on ECG devices structurally configured to discriminate between an ECG wave of a non-athlete and an ECG wave of a trained athlete followed by an appropriate interpretation of the ECG wave based on the discrimination to thereby minimize, if not prevent, high levels of false positive abnormal ECG interpretations of highly trained athletes.

For purposes of the present disclosure, the term "ECG device" broadly encompasses all stand-alone devices and multi-function system incorporated devices for generating ECG waves including, but not limited to:

(1) diagnostic ECG devices (e.g., PageWriter TC cardiographs, Efficia series of cardiograph);
(2) exercise ECG devices (e.g., ST80i stress testing system);
(3) ambulatory ECG devices (Holter monitor);
(4) bed-side monitoring ECG device (e.g., IntelliVue monitors, SureSigns monitors, and Goldway monitors);
(5) telemetry ECG device (e.g., IntelliVue MX40 monitor);
(6) advanced life support products (e.g., HeartStart MRx and HeartStart XL defibrillators, and Efficia DFM100 defibrillator/monitor); and
(7) ECG management system (e.g., IntelliSpace ECG management system).

Also for purposes of the present disclosure, (1) terms of the art including, but not limited to, "electrocardiogram" "cardiovascular condition", "heart beat", "heart rhythm", "morphology measurement", "ECG diagnostic criteria" and "electrode" are to be interpreted as understood in the art of the present disclosure and as exemplary described herein;

(2) the term "non-athlete" broadly encompasses, as understood in the art of the present disclosure and as exemplary described herein, any person lacking any measurable adaption of that person's ECG due to regular, intense exercising;

(3) the term "non-athletic ECG wave" broadly encompasses, as understood in the art of the present disclosure and as exemplary described herein, an ECG wave of a non-athlete;

(4) the term "non-athletic ECG diagnostic criteria" broadly encompasses, as understood in the art of the present disclosure and as exemplary described herein, ECG diagnostic criteria applied to a non-athletic ECG wave for purposes of detecting any abnormal cardiovascular conditions of the non-athlete;

(5) the term "normal non-athletic ECG wave" broadly encompasses, as understood in the art of the present disclosure and as exemplary described herein, an ECG wave of a non-athlete void of any indication of an abnormal cardiovascular condition (e.g., cardiomyopathies);

(6) the term "abnormal non-athletic ECG wave" broadly encompasses, as understood in the art of the present disclosure and as exemplary described herein, an ECG wave of a non-athlete indicative of one or more abnormal cardiovascular conditions (e.g., cardiomyopathies);

(7) the term "athlete" broadly encompasses, as understood in the art of the present disclosure and as exemplary described herein, any person having a measurable adaption of that person's ECG due to regular, intense exercising;

(8) the term "athletic ECG wave" broadly encompasses, as understood in the art of the present disclosure and as exemplary described herein, an ECG wave of an athlete;

(9) the term "athletic ECG diagnostic criteria" broadly encompasses, as understood in the art of the present disclosure and as exemplary described herein, ECG diagnostic criteria applied to an athletic ECG wave for purposes of detecting any abnormal cardiovascular condition of the athlete;

(10) the term "normal athletic ECG wave" broadly encompasses, as understood in the art of the present disclosure and as exemplary described herein, an ECG wave of an athlete void of any indication of an abnormal cardiovascular condition (e.g., cardiomyopathies);

(11) the term "abnormal non-athletic ECG wave" broadly encompasses, as understood in the art of the present disclosure and as exemplary described herein, an ECG wave of an athlete indicative of one or more abnormal cardiovascular conditions (e.g., cardiomyopathies);

(12) the term "classification feature" broadly encompasses, as understood in the art of the present disclosure and as exemplary described herein, a feature of an ECG wave suitable for discriminating between a non-athletic ECG wave and an athletic ECG wave. Examples of a classification feature of an ECG include, but are not limited to, a heart rate, a heart rhythm and a morphology measurement.

(13) the term "feature vector" broadly encompasses, as understood in the art of the present disclosure and as exemplary described herein, a n-dimensional vector of classification feature(s), $n \geq 1$;

(14) the term "objective athletic measurement" broadly encompasses, as understood in the art of the present disclosure and as exemplary described herein, a measurement of one or more athletic parameters indicative of a degree of athleticism of that person. Examples of the athletic parameter include, but are not limited to, a degree of athletic training over a specified period of time, a body fat percentage and a $VO_2$ max;

(15) the terms "comparatively estimate" and "comparatively estimating" broadly encompass, as understood in the art of the present disclosure and as exemplary described herein, a classification estimation derived from a comparative analysis of any aspect of an ECG wave (e.g., a feature vector of the ECG wave) for predicting an objective athletic measurement corresponding to the ECG wave. An example of a comparative analysis include, but are not limited to, an implementation of a waveform comparison function of the art and a vector comparison function of the art (e.g., an equality vector comparison function and near equality vector comparison function);

(16) the terms "regressively estimate" and "regressively estimating" broadly encompass, as understood in the art of the present disclosure and as exemplary described herein, a classification estimation derived from a regressive analysis of any aspect of an ECG wave (e.g., a feature vector of the ECG wave) for predicting an objective athletic measurement corresponding to the ECG wave. Examples of a regressive analysis include, but are not limited to, an implementation of a regressive equation, a quadratic discriminant, a support vector machine, a neural network, a decision tree, a random forest and a deep learning network;

(17) the term "controller" broadly encompasses all structural configurations, as understood in the art of the present disclosure and as exemplary described herein, of an application specific main board or an application specific integrated circuit for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s). The controller may be housed within or linked to an ECG device. Any descriptive labeling of a controller herein as an "electrocardiogram wave" controller, or an "electrocardiogram diagnostic" controller serves to identify a particular controller as described and claimed herein without specifying or implying any additional limitation to the term "controller";

(18) the term "application module" broadly encompasses a component of the controller consisting of an electronic circuit and/or an executable program (e.g., executable software and/or firmware) for executing a specific application. Any descriptive labeling of an application module herein (e.g., a "ECG wave classifier" module, and an "ECG wave interpreter") serves to identify a particular application module as described and claimed herein without specifying or implying any additional limitation to the term "application module"; and

(19) the term "output device" broadly encompasses, as understood in the art of the present disclosure and as exemplary described herein, a display, a printer, a speaker, light emitting diode (LED) indicator(s) or any other known device for visually and/or audibly communicating an ECG wave and/or any diagnosis of the ECG wave.

One form of the inventions of the present disclosure is an electrocardiogram diagnostic system having a non-athletic ECG diagnostic mode and an athletic ECG diagnostic mode. The electrocardiogram diagnostic system employs an electrocardiogram wave controller and an electrocardiogram diagnostic controller.

In operation, the electrocardiogram wave controller derives an ECG wave from one or more electrode signals. In response thereto, the electrocardiogram diagnostic controller classifies the ECG wave as either a non-athletic ECG wave or an athletic ECG wave, interprets a non-athletic classified ECG wave based on non-athletic ECG diagnostic criteria as either a normal non-athletic ECG wave or an abnormal non-athletic ECG wave, and interprets an athletic classified ECG wave based on athletic ECG diagnostic criteria as either a normal athletic ECG wave or an abnormal athletic ECG wave.

A second form of the inventions of the present disclosure is the electrocardiogram diagnostic controller employing a module in the form of an ECG wave classifier and an ECG wave interpreter.

In operation, the ECG wave classifier, responsive to receipt of an ECG wave, classifies the ECG wave as either non-athletic ECG wave or athletic ECG wave. The ECG wave interpreter interprets a non-athletic classified ECG wave based on non-athletic ECG diagnostic criteria as either a normal non-athletic ECG wave or an abnormal non-athletic ECG wave, and interprets an athletic classified ECG wave based on athletic ECG diagnostic criteria as either a normal athletic ECG wave or an abnormal athletic ECG wave.

A third form of the inventions of the present disclosure is a method of operating the electrocardiogram diagnostic controller between the non-athletic ECG diagnostic mode and the athletic ECG diagnostic mode.

The method involves the electrocardiogram diagnostic controller classifying an ECG wave as either non-athletic ECG wave or athletic ECG wave.

The method further involves the electrocardiogram diagnostic controller interpreting a non-athletic classified ECG wave based on non-athletic ECG diagnostic criteria as either a normal non-athletic ECG wave or an abnormal non-athletic ECG wave, and interpreting an athletic classified ECG wave based on athletic ECG diagnostic criteria as either a normal athletic ECG wave or an abnormal athletic ECG wave.

The foregoing forms and other forms of the inventions of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1:
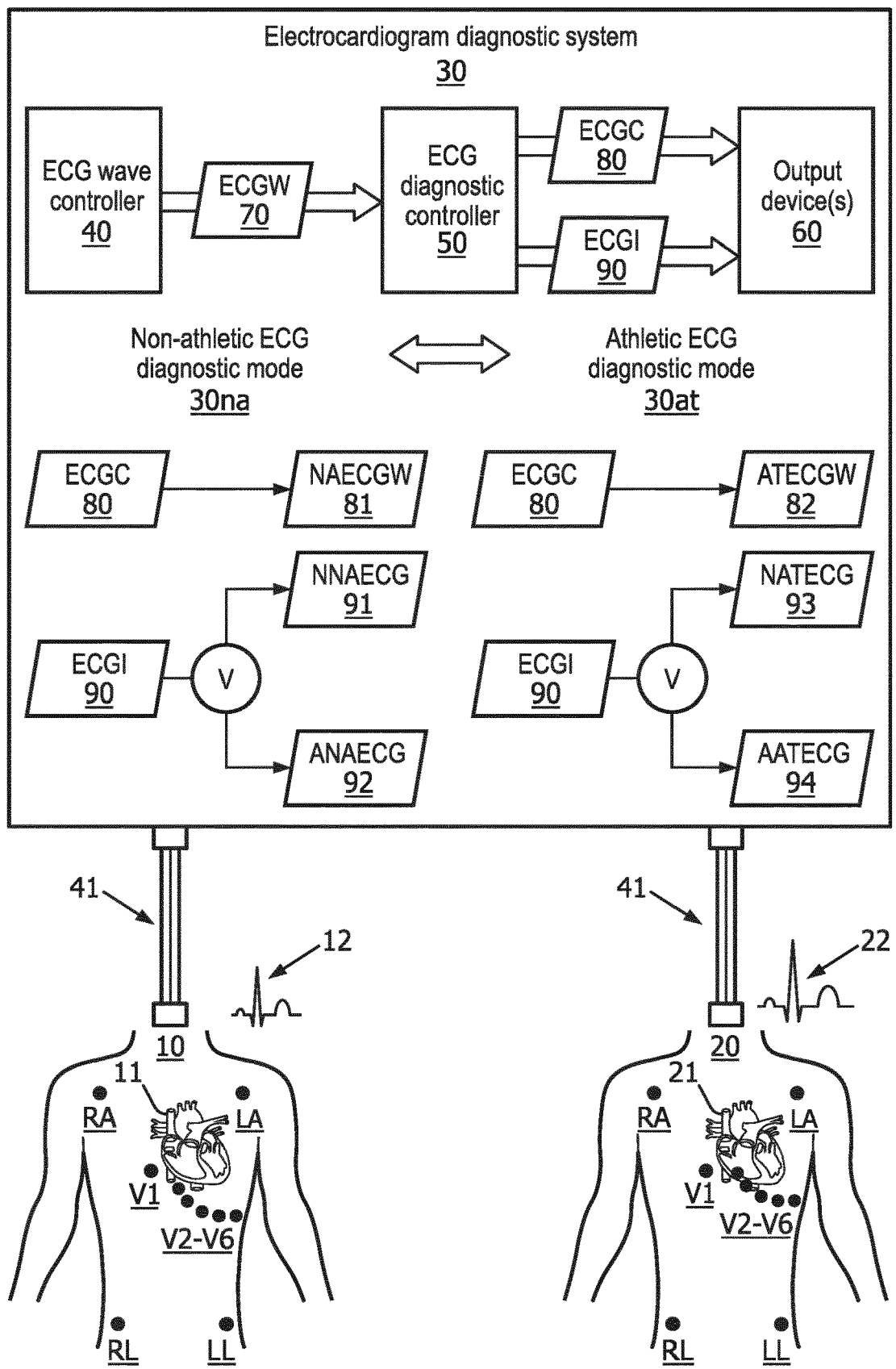
FIG. 1 illustrates an exemplary embodiment of an electrocardiogram diagnostic system for non-athletic/athletic ECG wave classification/interpretation in accordance with the inventive principles of the present disclosure.

To facilitate an understanding of the present disclosure, the following description of FIG. 1 teaches general inventive principles of an electrocardiogram diagnostic system for non-athletes and athletes. From this description, those having ordinary skill in the art will appreciate how to apply the general inventive principles of the present disclosure for making and using numerous and various embodiments of an electrocardiogram diagnostic system for non-athletes and athletes.

Referring to FIG. 1, an electrocardiogram diagnostic system 30 of the present disclosure employs an ECG wave controller 40, an ECG diagnostic controller 50 and one or more output devices 60 (e.g., a display, a printer, a speaker and/or LED indicator(s)). In practice, ECG wave controller 40 and ECG diagnostic controller 50 may be integrated or segregated as shown.

ECG wave controller 40 is linked to and/or incorporates any necessary hardware/software interface to a cable connector 41 for receiving electrode signals from a lead system connected to a non-athlete 10 or an athlete 20 (e.g., a standard 12-lead system, Mason-Likar lead system as shown or a reduced lead system like the EASI lead system).

Please note a heart 21 of athletic patient 20 is shown as being larger than a heart 11 of non-athletic patient 10 strictly to symbolize heart 21 typically will have ECG manifestations due to regular, intense training by athlete 20 (e.g., an increased vagal tone and an enlarged cardiac chamber).

ECG wave controller 40 further incorporates an ECG wave generator (not shown) as known in the art for controlling a generation of an ECG wave (ECGW) 70 from the electrode signals, such as, for example, an ECG wave 12 from the electrode signals of non-athlete 10 and an ECG wave 22 from the electrode signals of athlete 20.

ECG wave controller 40 communicates ECG wave 70 via wired and/or wireless channel(s) to ECG diagnostic controller 50 as shown and output device(s) 60.

ECG diagnostic controller 50 controls a transition of system 30 between a non-athletic ECG diagnostic mode 30na and an athletic ECG diagnostic mode 30at dependent upon whether ECG wave 70 is ECG wave 12 from the electrode signals of non-athlete 10 or ECG wave 22 from the electrode signals of athlete 20.

For non-athletic ECG diagnostic mode 30na, ECG diagnostic controller 50 classifies ECG wave 70 as a non-athletic ECG wave (NAECGW) 81 based on a detection by ECG diagnostic controller 50 that ECG wave 70 is ECG wave 12 from the electrode signals of non-athlete 10 as will be further exemplary described herein. Upon such classification, ECG diagnostic controller 50 diagnostically interprets non-athletic ECG wave 81 based on non-athletic ECG diagnostic criteria as a normal non-athletic ECG wave (NNAECG) 91 or as an abnormal non-athletic ECG wave (ANAECG) 92 as will be further exemplary described herein.

For athletic ECG diagnostic mode 30at, ECG diagnostic controller 50 classifies ECG wave 70 as an athletic ECG wave (ATECGW) 82 based on a detection by ECG diagnostic controller 50 that ECG wave 70 is ECG wave 22 from the electrode signals of athlete 20 as will be further exemplary described herein. Upon such classification, ECG diagnostic controller 50 diagnostically interprets athletic ECG wave 82 based on athletic ECG diagnostic criteria as a normal athletic ECG wave (NATECGW) 93 or as an abnormal athletic ECG wave (AATECG) 94 as will be further exemplary described herein.

ECG diagnostic controller 50 communicates an ECG report informative of an ECG classification (ECGC) 80 of ECG wave 70 and/or an ECG interpretation (ECCI) 90 of ECG wave 70 via wired and/or wireless channel(s) to output device(s) 60. In practice, a form or forms of the ECG report (e.g., textual, graphical, audible and/or visual) is dependent upon a type of output device 60 or types of output devices 60 being employed by system 30.

For example, ECG wave 70 may be displayed or printed with textual and/or graphical information corresponding to a classification and/or an interpretation of ECG wave 70.

Examples of displayed or printed information include, but are not limited to, (1) A declaration that the "ECG indicates non-athlete" or the "ECG indicates athletic training";

(2) A probability that the subject is an athlete, particularly a highly trained athlete;

(3) An estimation of any athletic training (e.g., number of hours per week of training);

(4) Specific ECG evidence for high probability of athletic training;

(5) ECG interpretation statements for normalities or abnormalities given ECG diagnostic criteria for a non-athlete or ECG diagnostic criteria for an athlete; and (6) ECG interpretation statements for normal variants due to athletic training.

Figure 2:
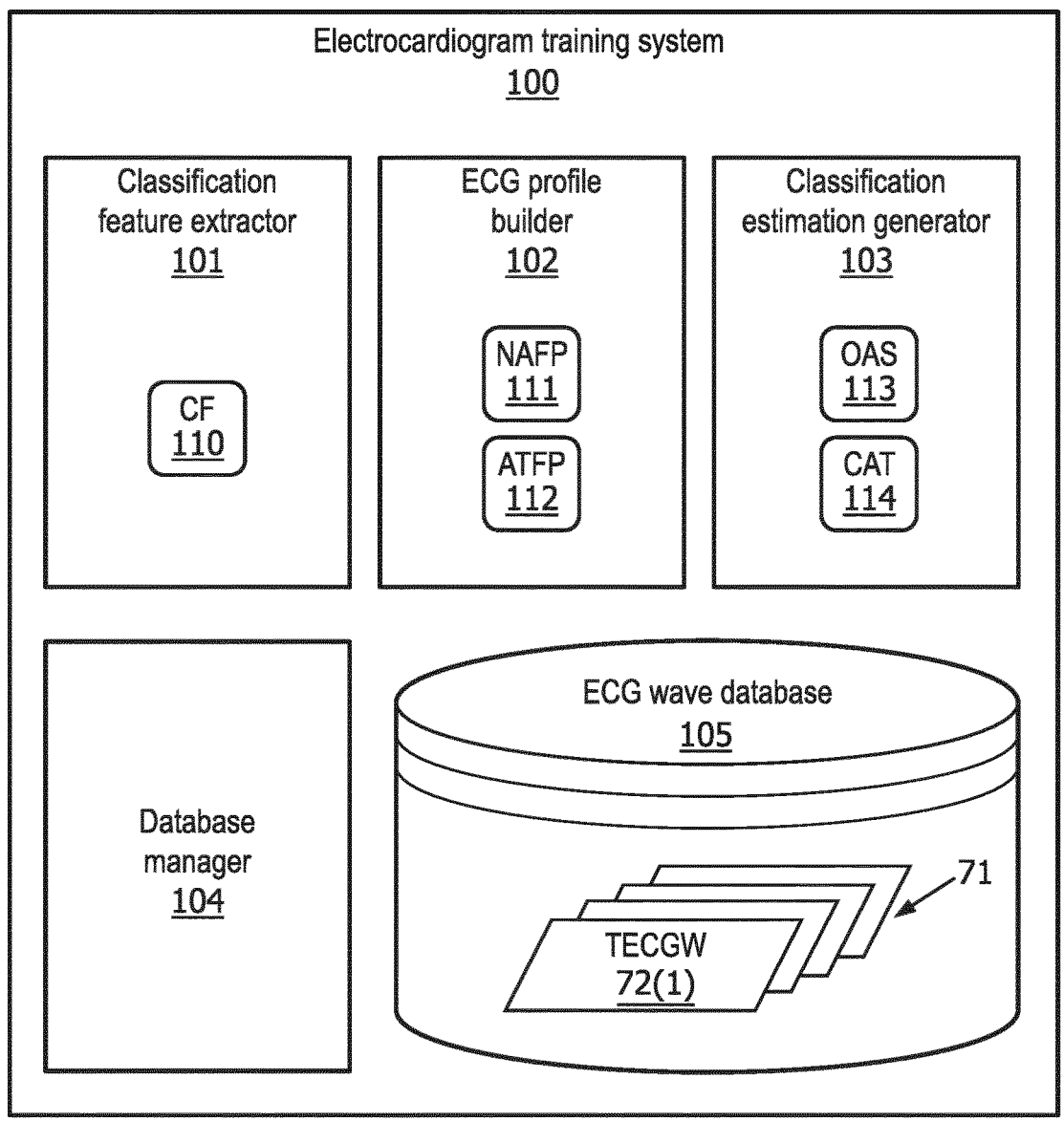
FIG. 2 illustrates an exemplary embodiment of an electrocardiogram training system for athletic detection in accordance with the inventive principles of the present disclosure.
Figure 3:
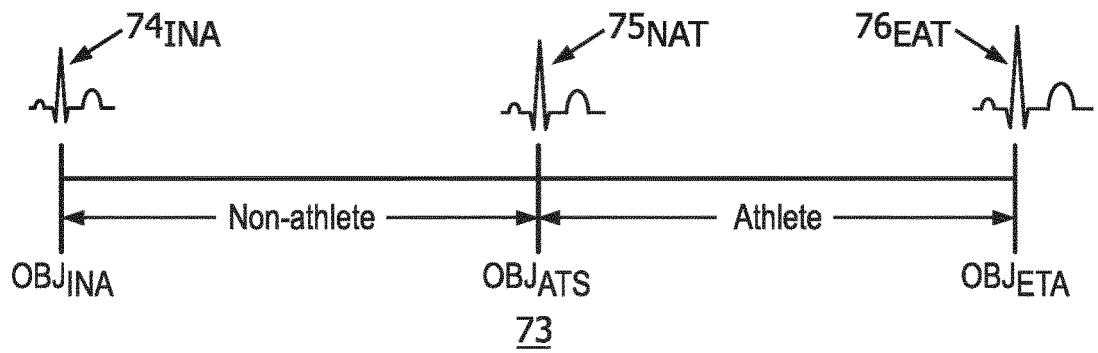
FIG. 3 illustrates an exemplary embodiment of objective athletic scale in accordance with the inventive principles of the present disclosure.

To facilitate a further understanding of the present disclosure, the following description of FIGS. 2 and 3 teaches inventive principles of an electrocardiogram training system for training an electrocardiogram diagnostic controller of the present disclosure in distinguishing between a non-athletic ECG wave and an athletic ECG wave. From this description, those having ordinary skill in the art will appreciate how to apply the inventive principles of the present disclosure for making and use numerous and various embodiments of an electrocardiogram training system of the present disclosure.

Referring to FIG. 2, electrocardiogram training system 100 (FIG. 1) includes a classification feature extractor 101, an ECG profile builder 102, and a classification methodology developer 103. For training purposes, electrocardiogram diagnostic training system 100 may further employ a database manager 104 and an ECG wave database 105 as shown, or alternatively be in communication with database manager 104 for purposes of accessing ECG wave database 105.

ECG wave database 105 stores a set 71 of varied training ECG waves (TECGW) 72 as managed by database manager 104 with each training wave including one or more cardiac cycles. As shown in FIG. 3, ECG waves 72 range on a ECG wave scale 73 extending between an ECG wave $74_{INA}$ of an inactive non-athlete (INA) and an ECG wave $76_{ETA}$ of an extremely trained athlete (ETA) with a midline ECG wave $75_{ATS}$ representative of an athletic transitional state (ATS) between an active non-athlete and an amateur athlete.

A premise of the inventions of the present disclosure is a training ECG wave 72 corresponding to ECG wave $74_{INA}$ or is located between ECG wave $74_{INA}$ and ECG wave $75_{ATS}$ is deemed a non-athletic ECG wave. Conversely, any training ECG wave 72 corresponding to ECG wave $76_{ETA}$ or is located between ECG wave $75_{ATS}$ and ECG wave $76_{ETA}$ is deemed an athletic ECG wave. Any training ECG wave 72 corresponding to ECG wave $75_{ATS}$ may be deemed by default a non-athletic ECG wave or an athletic ECG wave.

To identify a location of a training of ECG wave 72 on an objective athletic scale 73, the inventions of the present disclosure associates an objective athletic measurement OBJ of one or more athletic parameter(s) with each training ECG wave 72. As such, as shown in FIG. 3, any training ECG wave 72 associated with an objective athletic measurement with corresponding to objective athletic measurement $OBJ_{INA}$ or is located between objective athletic measurement $OBJ_{INA}$ and-objective athletic measurement $OBJ_{ATS}$ is deemed a non-athletic ECG wave. Conversely, any training ECG wave 72 associated with an objective athletic measurement corresponding to objective athletic measurement $OBJ_{ETA}$ or is located between objective athletic measurement $OBJ_{ATS}$ and objective athletic measurement $OBJ_{ETA}$ is deemed an athletic ECG wave. Any training ECG wave 72 associated with an objective athletic measurement corresponding to objective athletic measurement $OBJ_{ATS}$ may be deemed by default a non-athletic ECG wave or an athletic ECG wave.

For example, based an objective athletic measurement of intense physical training:
(1) an objective athletic measurement $OBJ_{INA}$ of approximately zero (0) daily hours of any type of intense physical activity may be associated with ECG wave $74_{INA}$;
(2) an objective athletic measurement $OBJ_{ATS}$ of four (4) hours of weekly intense physical training may be associated with ECG wave $75_{ATS}$; and
(3) an objective athletic measurement $OBJ_{ETA}$ of four (4) or more hours of daily intense physical training may be associated with ECG wave $76_{ETS}$.

As such, a training ECG wave 72 associated with an objective athletic measurement of less than four (4) hours of weekly intense physical training is deemed a non-athletic ECG wave. Conversely, any training ECG wave 72 associated with an objective athletic measurement of greater than four (4) hours of weekly intense physical training is deemed an athletic ECG wave. Any training ECG wave 72 associated with an objective athletic measurement of exactly four (4) hours of weekly intense physical training may be deemed by default a non-athletic ECG wave or an athletic ECG wave.

Also by example, based on an objective athletic measurement of body fat percentage:
(1) an objective athletic measurement $OBJ_{INA}$ of a body fat percentage indicative of obese person (e.g., body fat %≥25 for men and body fat %≥34 for women) may be associated with ECG wave $74_{INA}$;
(2) an objective athletic measurement $OBJ_{ATS}$ of a body fat percentage indicative of an average person (e.g., a body fat % of 18% for men and a body fat percentage 25 for women) may be associated with ECG wave $75_{ATS}$; and
(3) an objective athletic measurement $OBJ_{ETA}$ of a body fat percentage indicative of an athletic person (e.g., a body fat %≤6 for men and body fat %≤14 for women) may be associated with ECG wave $76_{ETA}$.

As such, a training ECG wave 72 associated with an objective athletic measurement of more than 18% body fat for men and more than 25% body fat for women is deemed a non-athletic ECG wave. Conversely, any training ECG wave 72 associated with an objective athletic measurement of less than 18% body fat for men and less than 25% body fat for women is deemed an athletic ECG wave. Any training ECG wave 72 associated with an objective athletic measurement of exactly 18% body fat for men and exactly 25% body fat for women may be deemed by default a non-athletic ECG wave or an athletic ECG wave.

By further example, based on an objective athletic measurement of VO2 max:
(1) an objective athletic measurement $OBJ_{ETA}$ of a $VO_2$ max indicative of poorly trained person of a particular age range (e.g., a $VO_2$ max<33 for men between 20-39 years old and a $VO_2$ max<23.6 for women between 20-29 years old) may be associated with ECG wave $74_{INA}$;
(2) an objective athletic measurement $OBJ_{ATS}$ of a VO2 max indicative of an average trained person of a particular age range (e.g., a $VO_2$ max of 42 for men between 20-39 years old and a $VO_2$ Max of 33 for women between 20-29 years old) may be associated with ECG wave $75_{ATS}$; and
(3) objective athletic measurement $OBJ_{ETA}$ of a VO2 max indicative of a superior trained person of a particular age range (e.g., a $VO_2$ max>52.4 for men between 20-39 years old and a $VO_2$ Max>41 for women between 20-29 years old) may be associated with ECG wave $76_{ETA}$.

As such, a training ECG wave 72 associated with an objective athletic measurement of a $VO_2$ max<42 for men and a $VO_2$ max<33 for men for women is deemed a non-athletic ECG wave. Conversely, any training ECG wave 72 associated with an objective athletic measurement of a $VO_2$ max>42 for men and a $VO_2$ max>33 for men for women is deemed an athletic ECG wave. Any training ECG wave 72 associated with an objective athletic measurement of a $VO_2$ max of 42 for men and a $VO_2$ max of 33 for men for women may be deemed by default a non-athletic ECG wave or an athletic ECG wave.

By even further example, an objective athletic measurement may be inclusive of two or more athletic parameters (e.g., intense physical training, body fat percentage, $VO_2$ max and any other suitable athletic parameter) whereby the athletic parameters are scored to yield a composite objective athletic measurement of an athletic transitional state (ATS) between an active non-athlete and an amateur athlete.

Referring back to FIG. 2, classification feature extractor 101 is structurally configured with hardware, software and/or firmware to extract a n number of classification features (CF) 110 from a single cardiac cycle or averaged cardiac cycle of each training ECG wave 72 as will be further exemplary described herein, $n \geq 1$.

ECG profile builder 102 is structurally configured with hardware, software and/or firmware to build a non-athletic feature profile (NAFP) 113 inclusive of an objective athletic measurement corresponding to a training ECG wave 72 and/or classification features thereof associated with a non-athlete as will be further exemplary described herein, and to build an athletic feature profile (ATFP) 113 inclusive of an objective athletic measurement corresponding to a training ECG wave 72 and/or classification features thereof associated with an athlete as will be further exemplary described herein.

Classification estimation generator 103 is structurally configured with hardware, software and/or firmware to derive, autonomously or user-interface driven, a classification estimator from an objective athletic scale (OAS) 113 (e.g., objective athletic scale 73 of FIG. 3) and a classification analysis technique (CAT) 114 (e.g., a comparative analysis or a regressive analysis) as will be further exemplary described herein.

To facilitate a further understanding of the present disclosure, the following description of FIGS. 4-6B teaches inventive principles of an electrocardiogram classification training method of the present disclosure. From this description, those having ordinary skill in the art will appreciate how to apply the inventive principles of the present disclosure for making and use numerous and various embodiments of an electrocardiogram classification training method of the present disclosure.

Figure 4:
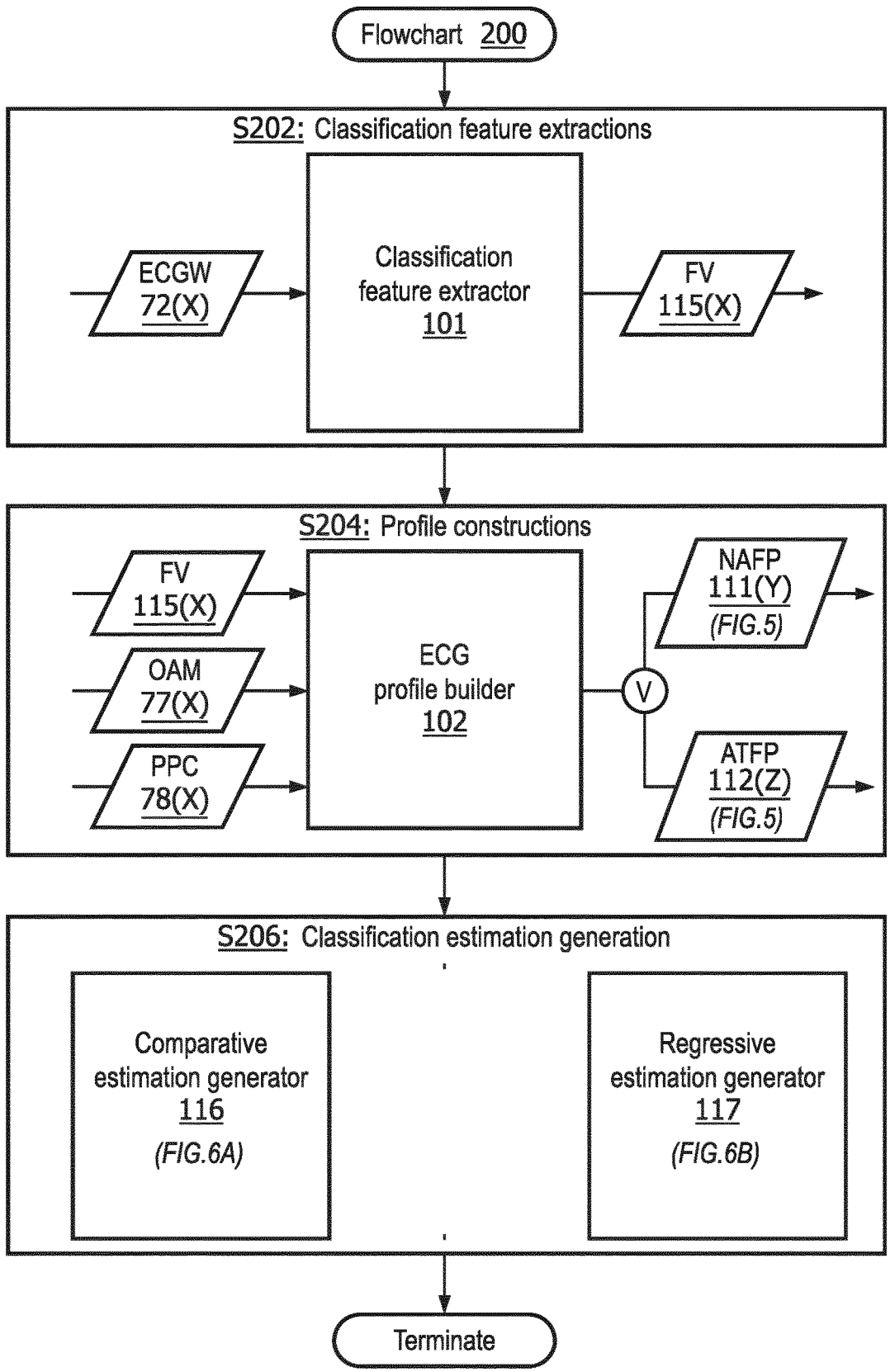
FIG. 4 illustrates a flowchart representative of an exemplary embodiment of an electrocardiogram athletic detection training method in accordance with the inventive principles of the present disclosure.

Referring to FIG. 4, a flowchart 200 is representative of an electrocardiogram classification training method of the present disclosure executed by electrocardiogram diagnostic training system 100 (FIG. 2) for training a classification estimator to distinguish between a non-athletic ECG wave and an athletic ECG wave derived from a vast number of training ECG waves 72.

Referring to FIGS. 2 and 4, in practice, training ECG set 71 will typically include thousands, even millions, of training ECG waves 72 with a large variation in physical activity ranging between inactive non-athletes (e.g., ECG wave $74_{INA}$ of FIG. 3) and extremely trained athletes (e.g., ECG wave $76_{ETA}$ of FIG. 3). Flowchart 200 facilitates a division of training ECG waves 72 into a non-athletic ECG wave grouping and an athletic ECG wave grouping with a dividing line being an athletic transitional state between an active non-athlete and an amateur athlete (e.g., ECG wave $75_{ATS}$ of FIG. 3). Additionally, in practice, flowchart 200 may be executed to further divide the non-athletic ECG wave grouping into sub-groups representative of physical activity variations between inactive non-athletes and active non-athletes, and to further divide the athletic ECG wave grouping into sub-groups representative of physical activity variations between amateur athletes and extremely trained athletes.

Still referring to FIGS. 2 and 4, a stage S202 of flowchart 200 encompasses, for each training ECG wave 72(X) of training ECG set 71, an extraction by classification feature extractor 101 of an n number of classification feature(s) 110 from a single cardiac cycle or an averaged cardiac cycle into a feature vector 115(X), $n \geq 1$.

In practice, classification feature(s) 110 may include a heart rate and/or a heart rhythm associated with a training ECG wave 72(X), and/or morphology measurement(s) of a training ECG wave 72(X).

Examples of direct morphology measurements include, but are not limited to, (1) a wave duration measurement (e.g., a P-wave duration, a PR interval, a QRS duration and a QT interval), (2) a wave amplitude measurement (e.g., a P-wave amplitude, a Q-wave amplitude, a R-wave amplitude, a S-wave amplitude, ST-segment amplitude and a T-wave amplitude), and (3) an electrical axis measurement (e.g., a P-wave axis, a QRS complex axis, a ST-segment axis and a T-wave axis).

Examples of predictive morphology measurements include, but are not limited to, a Sokolow-Lyon left ventricular hypertrophy (LVH) voltage and a Cornell LVH voltage.

Still referring to FIGS. 2 and 4, a stage S204 of flowchart 200 encompasses, for each training ECG wave 72(X) of training ECG set 71, a construction by ECG profile builder 102 of an non-athletic ECG profile (NAFP) 111 or an athletic ECG feature profile (ATFP) 112 from:

(1) a feature vector (FV) 112(X) extracted by classification feature extractor 101 during stage S202;

(2) objective athletic measurement (OAM) 77(X) of one or more athletic parameter(s) of a training subject X associated with a training ECG wave 72(X) (e.g., a degree of physical training, a body fat % and a $VO_2$ max); and (3) optional patient physical characteristic(s) (PPC) 78(X) of a training subject X associated with each training ECG wave 72 (e.g., age, gender, ethnicity, family history of heart disease, etc.).

Figure 5:
FIG. 5 illustrates exemplary embodiments of a non-athletic ECG profile and an athletic ECG profile in accordance with the inventive principles of the present disclosure.

For example, for each training ECG wave 72(X) associated with an objective athletic measurement 77(X) indicating a non-athletic training subject X based on objective athletic scale 113 as previously exemplary described herein, ECG profile builder 102 constructs a non-athletic feature profile 111 as shown in FIG. 5 detailing a non-athletic objective athletic measurement 77na, patient physical characteristic(s) 78 (if applicable) and a non-athletic feature vector 115na. Non-athletic feature profile 111 may be inclusive of a respective corresponding training ECG wave concurrent with non-athletic feature vector 115na or alternative to non-athletic feature vector 115na for embodiments of electrocardiogram classification training method of the present disclosure omitting classification feature extraction stage S202 of flowchart 200.

Similarly, for each training ECG wave 72(X) associated with an objective athletic measurement 77(X) indicating an athletic training subject X based on objective athletic scale 113 as previously exemplary described herein, ECG profile builder 102 constructs an athletic feature profile 112 as shown in FIG. 5 detailing an athletic objective athletic measurement 77at, patient physical characteristic(s) 78 (if applicable) and an athletic feature vector 115at. Athletic feature profile 112 may be inclusive of a respective corresponding training ECG wave 72 concurrent with athletic feature vector 115at or alternative to non-athletic feature vector 115at for embodiments of electrocardiogram classification training method of the present disclosure omitting classification feature extraction stage S202 of flowchart 200.

Alternatively or concurrently to feature vectors 115(X), non-athletic feature profile 111(Y) and a single athletic feature profile 112(Z) may be inclusive of respective training ECG waves 72(X) Referring back to FIGS. 2 and 4, in practice, a Y number of constructed non-athletic feature profiles 111 may be stored in a memory component of an electrocardiogram diagnostic controller 50 (FIG. 1) with non-athletic objective athletic measurement 77na serving as an index as will be further exemplary described herein. Such storage of the constructed non-athletic profiles 111 may be as a single non-athletic group or as multiple non-athletic subgroups based on two or more patient physical characteristics 78 if applicable.

Similarly, in practice, a Z number of constructed athletic feature profiles 112 may be stored in a memory component of an electrocardiogram diagnostic controller 50 (FIG. 1) with athletic objective athletic measurement 77at serving as an index. Such storage of the constructed athletic profiles 112 may be stored as a single athletic group or as multiple athletic subgroups based on two or more patient physical characteristics 78 if applicable.

Still referring to FIGS. 2 and 4, a stage S206 of flowchart 200 encompasses a generation by classification estimation generator 103 of a classification generator for measuring a mathematical relationship between feature vectors 115(X) and objective athletic measurements 77(X) that serves to predict an objective athletic measurement of a diagnostic subject.

In practice, any known technique suitable for analyzing an ECG wave and/or classification features thereof may be employed by classification estimation generator 103 during stage S206 for predicting an objective athletic measurement of a diagnostic subject.

In one embodiment of stage S206, classification estimation generator 103 is a comparative estimation generator 116 employing a comparative analysis technique for generating a comparative estimator.

Figure 6A:
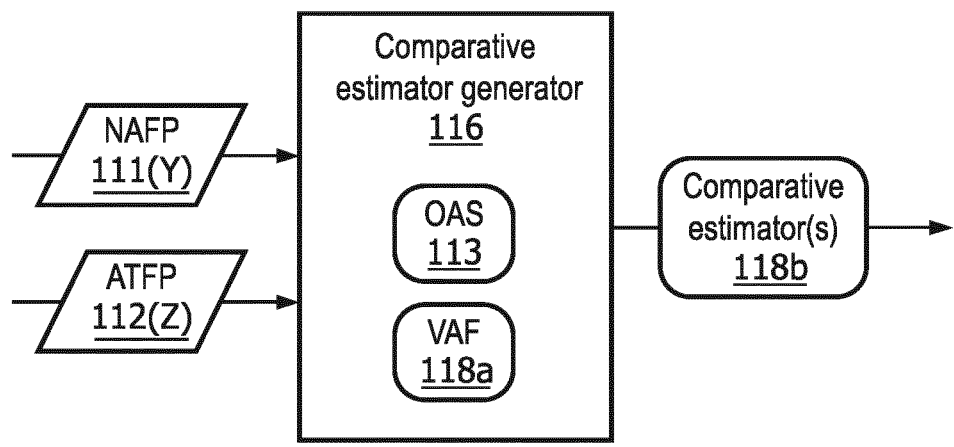
FIG. 6A illustrates exemplary embodiments of a comparative estimator in accordance with the inventive principles of the present disclosure.

For example, as shown in FIG. 6A, comparative estimation generator 116 processes the feature vectors 115(X) and objective athletic measurements 77(X) of non-athletic feature profile 111(Y) and athletic feature profile 112(Z) to ascertain, confirm or revise a midline of objective athletic scale 113, and generates one or more vector comparative estimators 118b with each comparative estimator 118b employing a vector comparative function (VAF) 118a (e.g., an equality vector comparison function and near equality vector comparison function).

For a single grouping of non-athletic feature profiles 111(Y) and athletic feature profiles 112(Z), comparative estimation generator 116 generates a single comparative estimator 118b for estimating a classification of a ECG wave of a diagnostic subject by comparing a feature vector of the diagnostic subject to each feature vectors 115(X) of non-athletic feature profiles 111(Y) and athletic feature profiles 112(Z) in accordance with vector comparative function (VAF) 118 to thereby deem an objective athletic measurement of the diagnostic subject as an objective athletic measurement 77(X) associated with a closest matching feature vector 115(x).

For multiple subgroupings of non-athletic feature profiles 111(Y) and athletic feature profiles 112(Z) as previously exemplary described herein, comparative estimation generator 116 generates a comparative estimator 118b per each subgroup for estimating a classification of a ECG wave of a diagnostic subject by comparing a feature vector of the diagnostic subject of a particular subgroup (e.g., gender) to each feature vectors 115(X) of non-athletic feature profiles 111(Y) and athletic feature profiles 112(Z) of the particular subgroup in accordance with vector comparative function (VAF) 118 to thereby deem an objective athletic measurement of the diagnostic subject as an objective athletic measurement 77(X) associated with a closest matching feature vector 115(x) of the particular subgroup.

As previously described herein, alternative or concurrent to feature vectors 115(X), non-athletic feature profile 111(Y) and a single athletic feature profile 112(Z) may be inclusive of respective training ECG waves 72. Accordingly, for this embodiment, comparative estimation generator 116 generates one or more comparative estimators 118b with each comparative estimator 118b employing a waveform comparative function (not shown) involving a timing alignment of a single cardiac cycle or a leading cardiac cycle.

For a single grouping of non-athletic feature profiles 111(Y) and athletic feature profiles 112(Z), comparative estimation generator 116 generates a single comparative estimator 118b for estimating a classification of a ECG wave of a diagnostic subject by comparing a ECG wave of the diagnostic subject to timing aligned training ECG waves 72(X) of non-athletic feature profiles 111(Y) and athletic feature profiles 112(Z) in accordance with the waveform comparative function to thereby deem an objective athletic measurement of the diagnostic subject as an objective athletic measurement 77(X) associated with a closest matching training ECG wave 72.

For multiple subgroupings of non-athletic feature profiles 111(Y) and athletic feature profiles 112(Z) as previously exemplary described herein, comparative estimation generator 116 generates a comparative estimator 118b per each subgroup for estimating a classification of a ECG wave of a diagnostic subject by comparing an ECG wave of the diagnostic subject of a particular subgroup (e.g., gender) to each timing aligned training ECG waves 72(X) of non-athletic feature profiles 111(Y) and athletic feature profile 112(Z) of the particular subgroup in accordance with waveform comparative function to thereby deem an objective athletic measurement of the diagnostic subject as an objective athletic measurement 77(X) associated with a closest matching training ECG wave 72.

Referring back to FIG. 4, in a second embodiment of stage S206, classification estimation generator 103 is a regressive estimation generator 117 employing a regressive analysis technique for generating a regressive estimator.

Figure 6B:
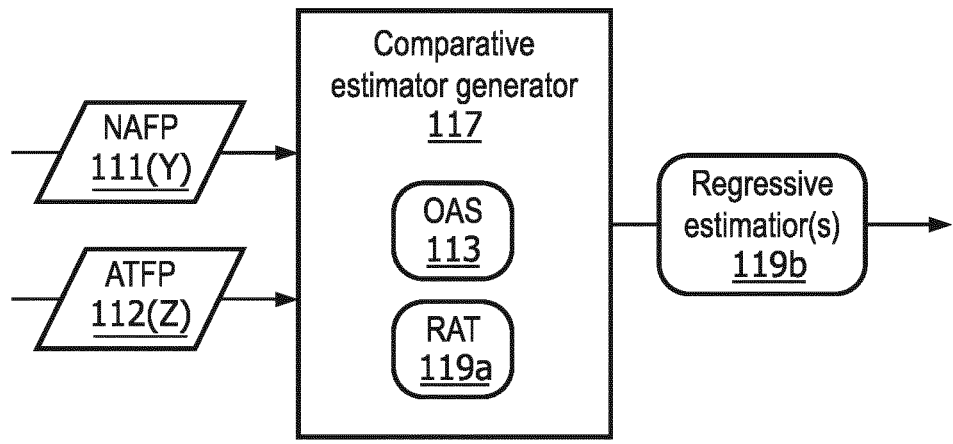
FIG. 6B illustrates exemplary embodiments of a regressive estimator in accordance with the inventive principles of the present disclosure.

For example, as shown in FIG. 6B, comparative estimation generator 116 processes the feature vectors 115(X) and objective athletic measurements 77(X) of non-athletic feature profile 111(Y) and athletic feature profile 112(Z) to generate one or more regressive estimators 119b with each regressive estimator 119b employing a regressive function (RAF) 119a (e.g., a regression equation, a quadratic discriminant, a support vector machine, a neural network, a decision tree, a random forest, and a deep learning network).

In one embodiment, regressive function 119a is an a regressive equation formulated from all feature vectors 115(X) in accordance with the following equation [1] for a n number of classification features 110, n≥1:

$$ATM = a + b_1 CF_1 + b_2 CF_2 + B_3 CF_3 + \ldots + B_n CF_n + u \quad [1]$$

where ATM is an objective athletic training measurement, CF is a classification feature, a is an intercept, b is a slope and u is a regression residual.

For a single grouping of non-athletic feature profiles 111(Y) and athletic feature profiles 112(Z), regressive estimation generator 117 generates a single regressive estimator 118b for estimating a classification of a ECG wave of a diagnostic subject by processing the feature vector of the diagnostic subject in accordance with regressive function 119a to output an objective athletic measurement of the diagnostic subject that is applied to objective athletic scale 113 to deem the ECG wave of the diagnostic subject as a non-athletic ECG wave or an athletic ECG wave.

For multiple subgroupings of non-athletic feature profiles 111(Y) and single athletic feature profiles 112(Z) as previously exemplary described herein, comparative estimation generator 116 generates a regressive estimator 119b per each subgroup for estimating a classification of a ECG wave of a diagnostic subject by processing a feature vector of the diagnostic subject of a particular subgroup (e.g., gender) in accordance with regressive function 119a to output an objective athletic measurement of the diagnostic subject of that particular subgroup that is applied to objective athletic scale 113 to deem the ECG wave of the diagnostic subject of the particular subgroup as a non-athletic ECG wave or an athletic ECG wave.

Flowchart 200 is terminated upon completion of stage S208. The resulting comparative estimator(s) 118b or regressive estimator(s) 119b is/are utilized for classifying ECG waves of diagnostic subjects as will be further exemplary described herein.

Figure 7:
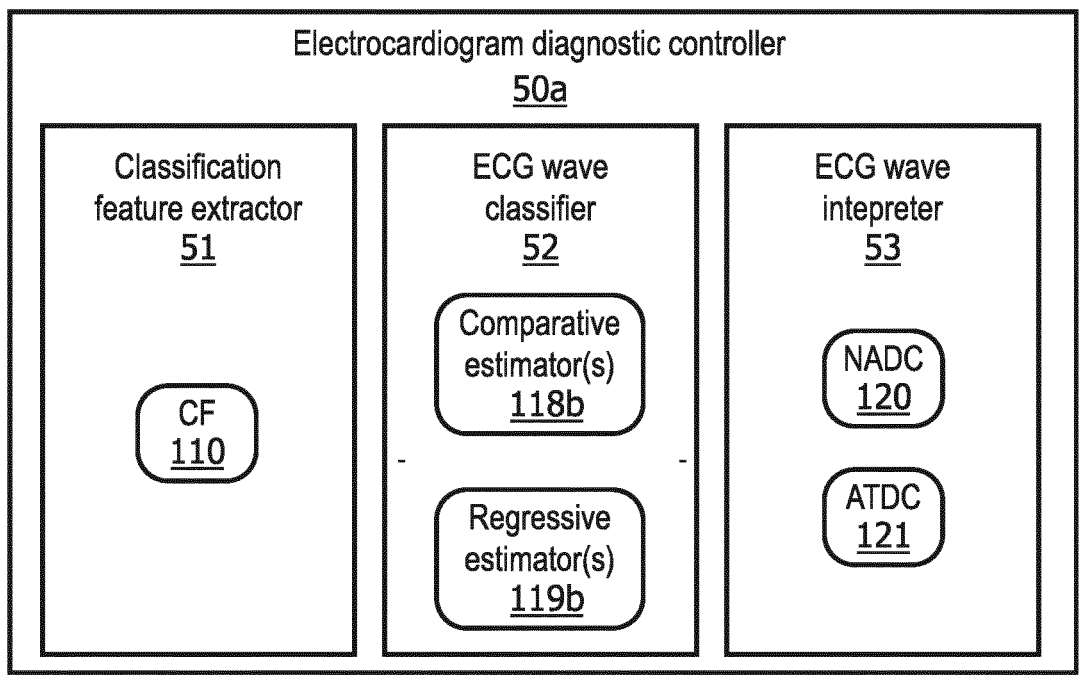
FIG. 7 illustrates an exemplary embodiment of an electrocardiogram diagnostic controller shown in FIG. 1 in accordance with the inventive principles of the present disclosure.
Figure 8:
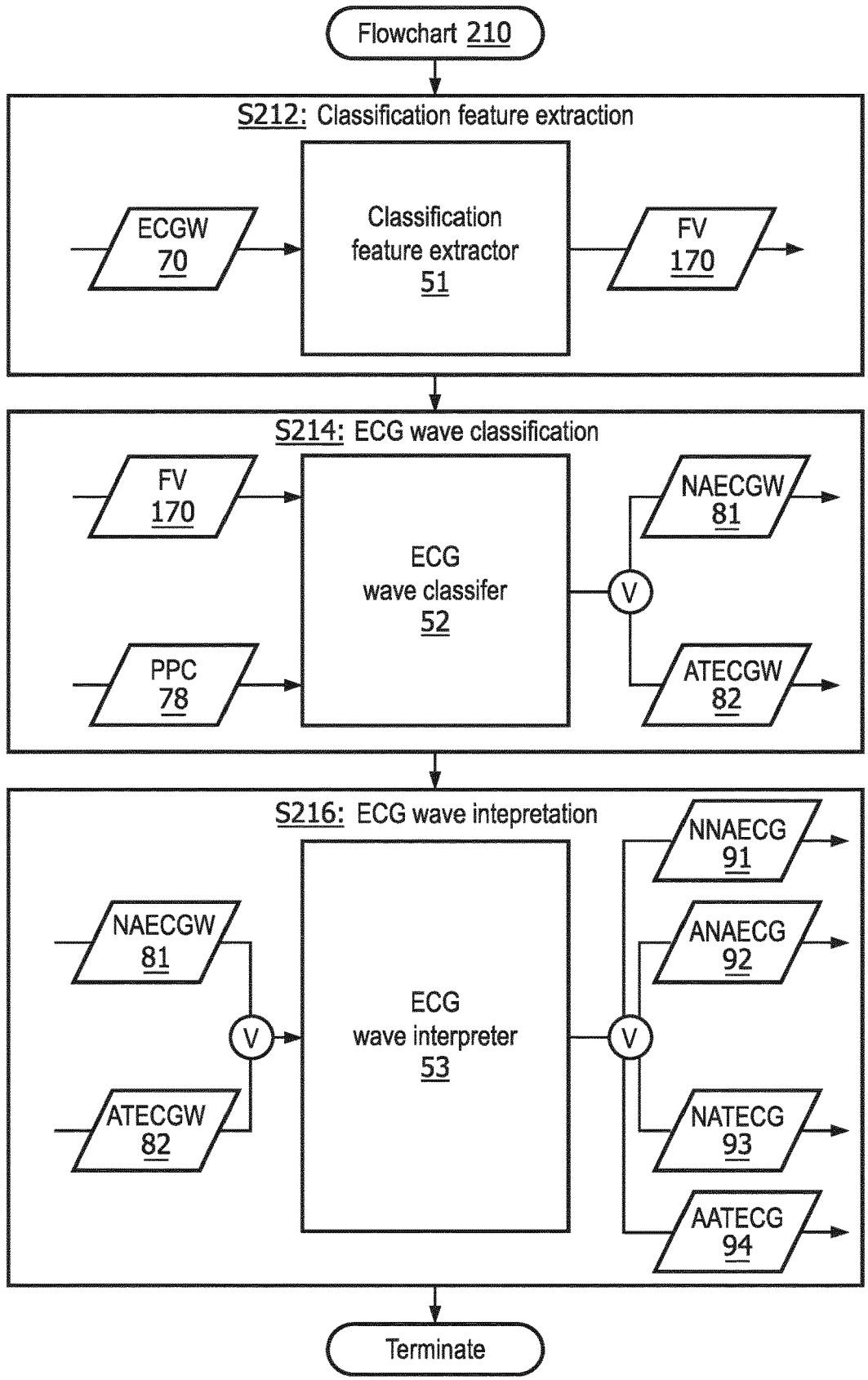
FIG. 8 illustrates a flowchart representative of an exemplary embodiment of an electrocardiogram classification/interpretation method in accordance with the inventive principles of the present disclosure.

To facilitate a further understanding of the present disclosure, the following description of FIGS. 7 and 8 teaches basic inventive principles of an electrocardiogram diagnostic controller of the present disclosure for classifying and interpreting an ECG wave. From this description, those having ordinary skill in the art will appreciate how to apply the inventive principles of the present disclosure for making and use numerous and various embodiments of an electrocardiogram diagnostic controller of the present disclosure.

Referring to FIG. 7, an embodiment 50a of electrocardiogram diagnostic controller 50 (FIG. 1) employs a classification feature extractor 51, an ECG wave classifier 52, and an ECG wave interpreter 53 for executing a flowchart 210 as shown in FIG. 8 that is representative of an electrocardiogram classification/interpretation method of the present disclosure for classifying and interpreting an ECG wave 70 (FIG. 1) for diagnostic purposes.

Classification feature extractor 51 is analogous to classification feature extractor 101 as previously exemplary described herein.

ECG wave classifier 52 embodies one or more comparative estimator(s) 118b, one or more regressive estimator(s) 119b and an objective athletic scale (not shown) (e.g., objective athletic scale 73 of FIG. 3) as previously exemplary described herein.

ECG wave interpreter 53 embodies non-athletic ECG diagnostic criteria (NAC) 120 and athletic ECG diagnostic criteria (ATC) 121 as further exemplary described herein.

Referring to FIGS. 7 and 8, a stage S212 of flowchart 210 encompasses an extraction by classification feature extractor 51 of classification feature(s) (CF) 110 from a ECG wave (ECGW) 70 into a feature vector (FV) 117 as previously exemplary described herein.

A stage S214 of flowchart 210 encompasses an execution by ECG wave classifier 52 of a comparative estimator 118b if embodied therein or a regressive estimator 119b as embodied therein with feature vector 117 as an input and patient physical characteristics 78 as an optional input as previously exemplary described herein to thereby classify ECG wave 70 as either non-athletic ECG wave (NAECGW) 81 or athletic ECG wave (ATECGW) 82.

For a classification of ECG wave 70 as non-athletic ECG wave 81 during stage S214, a stage S216 of flowchart 210 encompasses ECG wave interpreter 53 applying non-athletic ECG criteria 118 to non-athletic ECG wave 81 for diagnostically interpreting non-athletic ECG wave 81 as a normal non-athletic ECG wave (NNAECG) 91 or as abnormal non-athletic ECG wave (ANAECG) 92.

Examples of non-athletic ECG criteria 118 include, but are not limited to, normality/abnormality indicators as known in the art for non-athletes associated with sinus bradycardia, sinus arrhythmia, an ectopic atrial rhythm, a junctional escape rhythm, a 1° atrioventricular block and a Mobitz Type 1 2° atrioventricular block.

Further examples of non-athletic ECG criteria 118 include, but are not limited to, normality/abnormality morphology thresholds as known in the art for non-athletes associated with an incomplete right bundle branch block, isolated QRS voltage criteria for LVH, early repolarization (e.g., ST elevation, J-point elevation, J-waves or terminal QRS slurring), and convex ST segment elevation combined with T-wave inversion.

For a classification of ECG wave 70 as athletic ECG wave 82 during stage S214, stage S216 of flowchart 210 alternatively encompasses ECG wave interpreter 53 applying athletic ECG criteria 119 to athletic ECG wave 82 for diagnostically interpreting athletic ECG wave 82 as a normal athletic ECG wave (NATECG) 93 or as abnormal athletic ECG wave (AATECG) 94.

Examples of athletic ECG criteria 119 include, but are not limited to, normality/abnormality indicators as known in the art for athletes associated with sinus bradycardia, sinus arrhythmia, an ectopic atrial rhythm, a junctional escape rhythm, a 1° atrioventricular block and a Mobitz Type 1 2° atrioventricular block.

Further examples of athletic ECG criteria 119 include, but are not limited to, normality/abnormality morphology thresholds as known in the art for athletes associated with an incomplete right bundle branch block, isolated QRS voltage criteria for LVH, early repolarization (e.g., ST elevation, J-point elevation, J-waves or terminal QRS slurring), and convex ST segment elevation combined with T-wave inversion.

Flowchart 210 is terminated upon completion of stage S216. The result is a classified and interpreted ECG wave 70.

Referring back to FIG. 1, in practice, electrocardiogram diagnostic system 30 may be embodied in various forms.

Figure 9A:
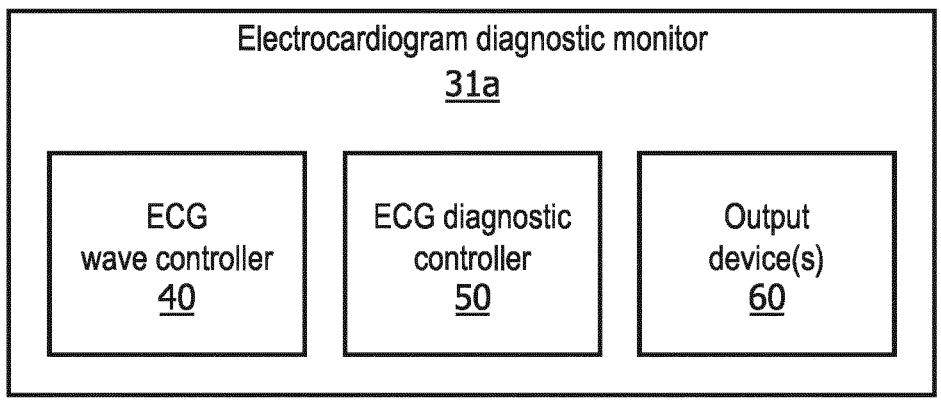
FIGS. 9A-9C illustrates exemplary embodiments of electrocardiogram diagnostic devices in accordance with the inventive principles of the present disclosure.

For example, FIG. 9A shows an electrocardiogram diagnostic monitor device 31a employing ECG wave controller 40, ECG diagnostic controller 50 and output device(s) 60. For device 31a, ECG wave controller 40 and ECG diagnostic controller 50 may be integrated or segregated.

Figure 9B:
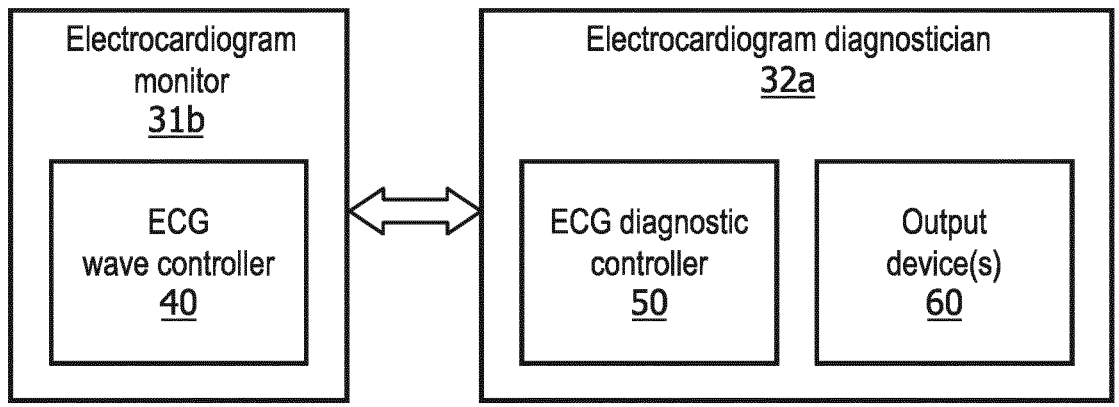

By further example, FIG. 9B shows an electrocardiogram monitor device 31b incorporating ECG wave controller 40, and an electrocardiogram diagnostician device 32a incorporating ECG diagnostic controller 50 and output device(s) 60.

Figure 9C:
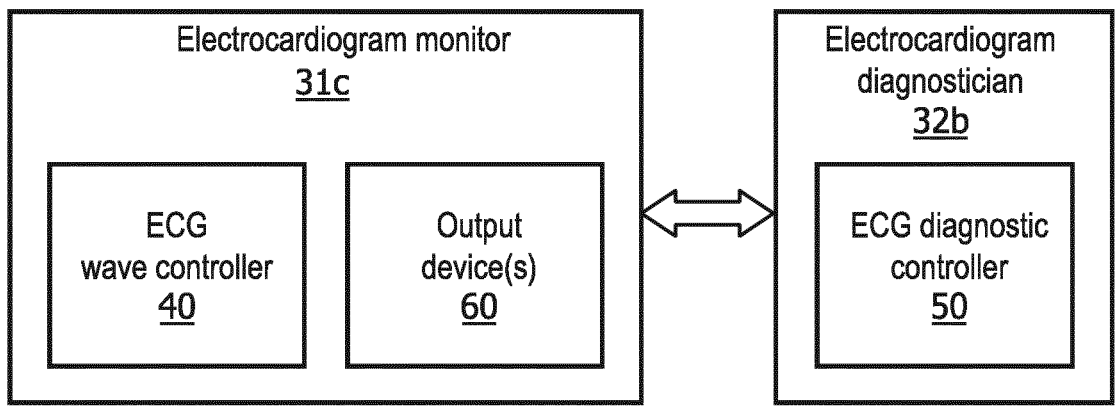

By even further example, FIG. 9C shows an electrocardiogram monitor device 31c incorporating ECG wave controller 40 and output device(s) 60, and an electrocardiogram diagnostician device 32b incorporating ECG diagnostic controller 50.

Referring to FIGS. 1-9, those having ordinary skill in the art will appreciate numerous benefits of the present disclosure including, but not limited to, a minimization, if not prevention, of false positive ECG interpretation for athletes, particularly highly trained athletes.

Furthermore, as one having ordinary skill in the art will appreciate in view of the teachings provided herein, features, elements, components, etc. described in the present disclosure/specification and/or depicted in the FIGS. 1-9 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 1-9 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive system and method for automatic classification/interpretation of ECG waves for non-athletes/athletes, (which embodiments are intended to be illustrative and not limiting), it is noted that modifications and variations can be made by persons having ordinary skill in the art in light of the teachings provided herein, including the FIGS. 1-9. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An electrocardiogram diagnostic system having a non-athletic ECG diagnostic mode and an athletic ECG diagnostic mode, the electrocardiogram diagnostic system comprising:
   an electrocardiogram wave controller structurally configured to generate an ECG wave responsive to at least one electrode signal; and
   an electrocardiogram diagnostic controller,
      wherein the electrocardiogram diagnostic controller is structurally configured, responsive to a generation of the ECG wave by the electrocardiogram wave controller, to classify the ECG wave as either a non-athletic ECG wave or an athletic ECG wave,
      wherein the electrocardiogram diagnostic controller is further structurally configured, responsive to a classification by the electrocardiogram diagnostic controller of the ECG wave as the non-athletic ECG wave, to interpret the ECG wave based on non-athletic ECG diagnostic criteria as either a normal non-athletic ECG wave or an abnormal non-athletic ECG wave, and
      wherein the electrocardiogram diagnostic controller is further structurally configured, responsive to a classification by the electrocardiogram diagnostic controller of the ECG wave as the athletic ECG wave, to interpret the ECG wave based on athletic ECG diagnostic criteria as either a normal athletic ECG wave or an abnormal athletic ECG wave.

2. The electrocardiogram diagnostic system of claim 1, wherein the electrocardiogram diagnostic controller is further structurally configured to generate an ECG report informative of at least one of:
   a classification by the electrocardiogram diagnostic controller of the ECG wave as either the non-athletic ECG wave or the athletic ECG wave; and
   an interpretation by the electrocardiogram diagnostic controller of the ECG wave as either the normal non-athletic ECG wave, the abnormal non-athletic ECG wave, the normal athletic ECG wave or the abnormal athletic ECG wave.

3. The electrocardiogram diagnostic system of claim 2, wherein the ECG report is informative of at least one abnormal cardiovascular condition associated with the interpretation by the electrocardiogram diagnostic controller of the ECG wave as either the abnormal non-athletic ECG wave or the abnormal athletic ECG wave.

4. The electrocardiogram diagnostic system of claim 2, further comprising:
an output device,
wherein the electrocardiogram diagnostic controller is further structurally configured, responsive to a generation of the ECG report by the electrocardiogram diagnostic controller, to broadcast the ECG report to the output device.

5. The electrocardiogram diagnostic system of claim 1, wherein the electrocardiogram diagnostic controller is further structurally configured to extract classification features from the ECG wave as a basis for classifying the ECG wave as either the non-athletic ECG wave or the athletic ECG wave.

6. The electrocardiogram diagnostic system of claim 5, wherein the classification features of the ECG wave include at least one of:
a heart rate of the ECG wave;
a heart rhythm of the ECG wave; and
at least one morphology measurement of the ECG wave.

7. The electrocardiogram diagnostic system of claim 1, wherein the electrocardiogram diagnostic controller is further structurally configured, responsive to an extraction of the classification features from the ECG wave by the electrocardiogram diagnostic controller, to comparatively estimate the ECG wave as either the non-athletic ECG wave or the athletic ECG wave.

8. The electrocardiogram diagnostic system of claim 1, wherein the electrocardiogram diagnostic controller is further structurally configured, responsive to an extraction of the classification features from the ECG wave by the electrocardiogram diagnostic controller, to regressively estimate the ECG wave as either the non-athletic ECG wave or the athletic ECG wave.

9. An electrocardiogram diagnostic controller for an electrocardiogram diagnostic system having a non-athletic ECG diagnostic mode and an athletic ECG diagnostic mode, the electrocardiogram diagnostic controller comprising:
an ECG wave classifier structurally configured, responsive to receipt of an ECG wave, to classify the ECG wave as either a non-athletic ECG wave or an athletic ECG wave; and
an ECG wave interpreter,
wherein the ECG wave interpreter is structurally configured, responsive to a classification by the ECG wave classifier of the ECG wave as the non-athletic ECG wave, to interpret the ECG wave based on non-athletic ECG diagnostic criteria as either a normal non-athletic ECG wave or an abnormal non-athletic ECG wave, and
wherein the ECG wave interpreter is further structurally configured, responsive to a classification by the ECG wave classifier of the ECG wave as an athletic ECG wave, to interpret the ECG wave based on athletic ECG diagnostic criteria as either a normal athletic ECG wave or an abnormal athletic ECG wave.

10. The electrocardiogram diagnostic controller of claim 9, wherein at least one of the ECG wave classifier and the ECG wave interpreter is structurally configured to generate an ECG report informative of at least one of:
a classification by the ECG wave classifier of the ECG wave as either the non-athletic ECG wave or the athletic ECG wave; and
an interpretation by the ECG wave interpreter of the ECG wave as either the normal non-athletic ECG wave, the abnormal non-athletic ECG wave, the normal athletic ECG wave or the abnormal athletic ECG wave.

11. The electrocardiogram diagnostic controller of claim 10, wherein the ECG report is informative of at least one abnormal cardiovascular condition associated with the interpretation by the ECG wave interpreter of the ECG wave as either the abnormal non-athletic ECG wave or the abnormal athletic ECG wave.

12. The electrocardiogram diagnostic controller of claim 9, wherein the ECG wave classifier is further structurally configured to extract classification features from the ECG wave as a basis for classifying the ECG wave as either the non-athletic ECG wave or the athletic ECG wave.

13. The electrocardiogram diagnostic controller of claim 12, wherein the classification features of the ECG wave include at least one of:
a heart rate of the ECG wave;
a heart rhythm of the ECG wave; and
at least one morphology measurement of the ECG wave.

14. The electrocardiogram diagnostic controller of claim 9, wherein the ECG wave classifier is further structurally configured, responsive to an extraction of the classification features from the ECG wave by the ECG wave classifier, to comparatively estimate the ECG wave as either the non-athletic ECG wave or the athletic ECG wave.

15. The electrocardiogram diagnostic system of claim 9, wherein the ECG wave classifier is further structurally configured, responsive to an extraction of the classification features from the ECG wave by ECG wave classifier, to regressively estimate the ECG wave as either the non-athletic ECG wave or the athletic ECG wave.

16. A method of operating an electrocardiogram diagnostic controller between a non-athletic ECG diagnostic mode and an athletic ECG diagnostic mode, the method comprising:
the electrocardiogram diagnostic controller classifying an ECG wave as either a non-athletic ECG wave or an athletic ECG wave;
responsive to a classification by the electrocardiogram diagnostic controller of the ECG wave as the non-athletic ECG wave, the electrocardiogram diagnostic controller operating in the non-athletic ECG diagnostic mode including the electrocardiogram diagnostic controller interpreting the ECG wave based on non-athletic ECG diagnostic criteria as either a normal non-athletic ECG wave or an abnormal non-athletic ECG wave; and
responsive to a classification by the electrocardiogram diagnostic controller of the ECG wave as the athletic ECG wave, the electrocardiogram diagnostic controller operating in the athletic ECG diagnostic mode including the electrocardiogram diagnostic controller interpreting the ECG wave based on athletic ECG diagnostic criteria as either a normal athletic ECG wave or an abnormal athletic ECG wave.

17. The method of claim 16, further comprising:
the electrocardiogram diagnostic controller generating an ECG report informative of at least one of:
a classification by the electrocardiogram diagnostic controller of the ECG wave as either the non-athletic ECG wave or the athletic ECG wave; and
an interpretation by the electrocardiogram diagnostic controller of the ECG wave as either the normal non-athletic ECG wave, the abnormal non-athletic ECG wave, the normal athletic ECG wave or the abnormal athletic ECG wave.

18. The method of claim 16, wherein the electrocardiogram diagnostic controller classifying the ECG wave as either the non-athletic ECG wave or the athletic ECG wave includes:
   the electrocardiogram diagnostic controller extracting classification features from the ECG wave as a basis for classifying the ECG wave as either the non-athletic ECG wave or the athletic ECG wave.

19. The method of claim 18, wherein the electrocardiogram diagnostic controller classifying the ECG wave as either the non-athletic ECG wave or the athletic ECG wave further includes:
   the electrocardiogram diagnostic controller comparatively estimating the ECG wave as either the non-athletic ECG wave or the athletic ECG wave.

20. The method of claim 18, wherein the electrocardiogram diagnostic controller classifying the ECG wave as either the non-athletic ECG wave or the athletic ECG wave includes:
   the electrocardiogram diagnostic controller regressively estimating the ECG wave as either the non-athletic ECG wave or the athletic ECG wave.

\* \* \* \* \*